United States Patent [19]

KenKnight

[11] Patent Number: 5,797,967
[45] Date of Patent: Aug. 25, 1998

[54] SYSTEM AND METHOD TO REDUCE DEFIBRILLATION REQUIREMENTS

[75] Inventor: Bruce H. KenKnight, Minneapolis, Minn.

[73] Assignee: Cardiac Pacemakers, Inc., St. Paul, Minn.

[21] Appl. No.: 720,360

[22] Filed: Sep. 27, 1996

[51] Int. Cl.⁶ .................................................. A61N 1/39
[52] U.S. Cl. ........................................................... 607/4
[58] Field of Search ................................ 607/5, 6, 7, 8, 607/4

[56] References Cited

U.S. PATENT DOCUMENTS

| | | | |
|---|---|---|---|
| 4,548,203 | 10/1985 | Tacker, Jr. et al. | 128/419 |
| 4,559,946 | 12/1985 | Mower | 128/419 D |
| 4,637,397 | 1/1987 | Jones et al. | 128/419 D |
| 4,641,656 | 2/1987 | Smits | 128/419 D |
| 4,693,253 | 9/1987 | Adams | 128/419 |
| 4,708,145 | 11/1987 | Tacker, Jr. et al. | 128/419 D |
| 4,763,646 | 8/1988 | Lekholm | 128/419 PG |
| 4,774,952 | 10/1988 | Smits | 128/419 D |
| 4,775,950 | 10/1988 | Terada et al. | 364/578 |
| 4,787,389 | 11/1988 | Tarjan . | |
| 4,788,980 | 12/1988 | Mann et al. | 128/419 PG |
| 4,800,883 | 1/1989 | Winstrom | 128/419 D |
| 4,821,723 | 4/1989 | Baker, Jr. et al. | 128/419 D |
| 4,827,932 | 5/1989 | Ideker et al. | 128/419 D |
| 4,834,100 | 5/1989 | Charms | 128/419 D |
| 4,944,300 | 7/1990 | Saksena | 128/419 |
| 4,984,572 | 1/1991 | Cohen | 128/419 D |
| 4,996,984 | 3/1991 | Sweeney | 128/419 D |
| 5,007,422 | 4/1991 | Pless et al. | 28/419 PG |
| 5,085,213 | 2/1992 | Cohen | 128/419 D |
| 5,111,812 | 5/1992 | Swanson et al. | 128/419 D |
| 5,154,485 | 10/1992 | Fleishman | 297/445 |
| 5,161,528 | 11/1992 | Sweeney | 128/419 D |
| 5,163,428 | 11/1992 | Pless | 128/419 D |
| 5,178,140 | 1/1993 | Ibrahim | 128/419 D |
| 5,265,600 | 11/1993 | Adams et al. | 607/4 |
| 5,275,621 | 1/1994 | Mehra | 607/5 |
| 5,282,836 | 2/1994 | Kreyenhagen et al. | 607/4 |
| 5,350,401 | 9/1994 | Levine | 607/4 |
| 5,366,485 | 11/1994 | Kroll et al. | 607/5 |
| 5,431,682 | 7/1995 | Hedberg | 607/5 |
| 5,441,521 | 8/1995 | Hedberg | 607/6 |
| 5,464,429 | 11/1995 | Hedberg et al. | 607/4 |
| 5,489,293 | 2/1996 | Pless et al. | 607/5 |
| 5,522,853 | 6/1996 | Kroll | 607/5 |

FOREIGN PATENT DOCUMENTS

| | | |
|---|---|---|
| 0467652 | 1/1992 | European Pat. Off. . |
| 0588124 | 3/1994 | European Pat. Off. . |
| 95/28987 | 11/1995 | WIPO . |
| 95/28988 | 11/1995 | WIPO . |
| 97/01373 | 1/1997 | WIPO . |

OTHER PUBLICATIONS

M. Allessie et al., "Regional Control of Atrial Fibrillation by Rapid Pacing in Conscious Dogs", *Circulation*, vol. 84, No. 4, 1689–1697, (Oct. 1991).

Gregory M. Ayers et al., "Ventricular Proarrhythmic Effects of Ventricular Cycle Length and Shock Strength in a Sheep Model of Transvenous Atrial Defibrillation", *Circulation*, vol. 89, No. 1, 413–422, (Jan. 1994).

(List continued on next page.)

*Primary Examiner*—Scott M. Getzow
*Attorney, Agent, or Firm*—Schwegman, Lundberg, Woessner, & Kluth, P.A.

[57] ABSTRACT

A hybrid tachyarrhythmia therapy utilizes a combination of two therapies: pacing therapy (optionally followed by therapy employing waveforms having morphologies congruent to defibrillation waveforms but at reduced-strength); and defibrillation (including cardioversion) therapy. The two therapies are applied in either a temporally coincident, or an immediately sequential, fashion. At least one pacing pulse that influences only a localized portion of selected cardiac tissue is applied, prior to or coincident with at least one defibrillation-level shock. The defibrillation shock strength (voltage and/or energy) required to terminate the tachyarrhythmia is less than would be required in the absence of the critically-coupled pacing pulses. The therapy may be applied to atrial or ventricular tachyarrhythmias. A variety of electrode configurations and defibrillation pulse schemes may be employed.

28 Claims, 7 Drawing Sheets

OTHER PUBLICATIONS

B. H. Kenknight et al., "Regional Capture of Fibrillating Ventricular Myocardium", *Circulation Research*, vol. 77, No. 4, 849–855, (Oct. 1995).

D. W. Frazier et al., "Stimulus–Induced Critical Point—Mechanism for Electrical Initiation of Reentry in Normal Canine Myocardium", *J. Clin. Invest.*, vol. 83, 1039–1052, (Mar. 1989).

A. S. Tang et al., "Three–Dimensional Potential Gradient Fields generated by Intercardiac Catheter and Cutaneous Patch Electrodes", *Circulation*, vol. 85, No. 5, 1857–1864 (May 1992).

S. M. Dillon, "Synchronized Repolarization After Defibrillation Shocks", *Circulation*, vol. 85, No. 5, 1865–1878, (May 1992).

J. M. Wharton et al., "Cardiac Potential and Potential Gradient Fields Generated by Single, Combined and Sequential Shocks During Ventricular Defibrillation", *Circulation*, vol. 85, No 4, 1510–1523, (Apr. 1992).

M Allessie, et al., "RegionalControl of Atrial Fibrillation by Rapid Pacing in Concious Dogs", *Circulation*, vol. 84, No. 4, 1689–1697, (Oct. 1991).

Gregory M Ayers, et al., "Ventricular Proarrhythmic Effects of Ventricular Cycle Length and Shock Strength in a Sheep Model of Transvenous Atrial Defibrillation", *Circulation*, vol. 89, No. 1, 413–422, (Jan. 1994).

B H KenKnight, et al., "Regional Capture of Fibrillating Venrticular Myocardium", *Circulation Research*vol. 77, No. 4, 849–855, (Oct. 1995).

D W Frazier, et al., "Stimulus–Induced Critical Point—Mechanism for Electrical Innitiation of Reentry in Normal Canine Myocardium", *J. Clin. Invest.*, vol. 83, 1039–1052, (Mar. 1989).

A S Tang, et al., "Three–Dimensional Potential Gradient Fields Generated by Intracardiac Catheter and Cutaneous Patch Electrodes", *Circulation*, vol. 85, No. 5, 1857–1864, (May 1992).

S M Dillon, "Synchronized Repolarization After Defibrillation Shocks", *Circulation*, vol. 85, No. 5, 1865–1878, (May 1992).

J M Wharton, et al., "Cardiac Potential and Potential Gradient Fields Generated by Single, Combined , and Sequential Shocks During Ventricular Defibrillation", *Circulation*, vol. 85, No. 4, 1510–1523, (Apr. 1992).

SYSTEM AND METHOD TO REDUCE DEFIBRILLATION REQUIREMENTS

BACKGROUND

The classic definition of defibrillation is simply the termination of fibrillation. Fibrillation is a condition in which rapidly changing wavefronts of myocardial activation circulate within heart tissue and prevent coordinated mechanical contractions of cardiac muscle as a whole, thus reducing or eliminating the hemodynamic benefit produced by the contractions. Normally, defibrillation is accomplished with transthoracic electrical shocks[1] in the range of approximately 100–400 joules; or shocks in the range of approximately 2–30 joules applied internally to the chest, either between a plurality of areal ("patch") electrodes, or between a plurality of endocardial catheter electrodes, the plurality of electrodes including at least one electrode located on or distant from the heart.

[1]The term "Pulse" is sometimes used interchangeably with "shock." Both are used here to denote either voltage or current discharge from an energy storage device, such as a capacitor or capacitor bank, as indicated by a plot of either voltage or current as a function of time.

In contrast to defibrillation, cardioversion therapy is applied during situations when heart rhythms are comparatively organized, but occurring too rapidly to allow hemodynamic stability. In these cases, cardioversion shocks are delivered at or very near the peak of the sensed ventricular depolarization (i.e., the QRS complex). Typical cardioversion shocks are in the range of approximately 50–200 joules if delivered transthoracically, or 0.05–2 joules if delivered internally.

Pacing pulses of the type used for bradycardia therapy or antitachycardia pacing are those which have energies on the order of microjoules, and thus are well below the energy level of defibrillation or cardioversion shocks.

The low conversion energy benefits of internal defibrillation are the basis of the commercially available system commonly known as the automatic implantable defibrillator (AID) and other similar names. Such systems are generally fully implantable and include a computer-controlled pulse generator to detect, diagnose, and treat hemodynamically unstable rhythms which spontaneously occur in patients. Typically, these systems sense the presence of a potentially lethal arrhythmia by continually monitoring rate and morphology features from sensed cardiac electrograms; diagnose known clinically treatable arrhythmias by comparing the rate and morphology features to pre-programmed and/or adaptive criteria; and deliver a high (up to approximately 40 Joules, depending on the manufacturer and model) shock to terminate the unfavorable rhythm and restore coordinated mechanical pumping function. The most advanced of the currently commercialized devices use a tiered therapy approach, in which a pre-programmed therapy is automatically selected, based on certain rhythm classification criteria. For example, slow, monomorphic, hemodynamically stable ventricular tachyarrhythmia (VT) may be treated with pacing (~40 microjoule) therapies, e.g., antitachyarrhythmia pacing (ATP), while fast, polymorphic, hemodynamically unstable rhythms may be treated with low strength (0.05–2 Joules) shocks followed by higher strength (2–40 Joules) shocks if earlier interventions fail. For primary ventricular fibrillation (VF), only high strength (typically at least 10 Joules) defibrillation shocks are prescribed. In general, the morphology of the defibrillation waveform affects the amount of energy needed for successful therapy. Biphasic shocks usually require less energy than monophasic shocks, although exceptions have been observed.

Experimental variations on these commercially available designs attempt to "pretreat" the arrhythmia, especially fibrillation, with electrical stimulation to metamorphose the arrhythmia into a more easily treated arrhythmia; or, at least into an arrhythmia which does not require as much of the limited energy available for clinically desirable attempts. For example, a successful pretreatment scheme would lower the energy subsequently used in a defibrillation attempt from approximately 20–40 Joules to approximately 10 Joules. If the attempt is successful at the lower energy level, side effects (i.e., pain, long term damage to the myocardium, etc.) are minimized. Even if the defibrillation attempt is not successful, the reduction in energy helps ensure that adequate energy from the limited battery supply is available for a subsequent, higher energy attempt.

The first comprehensive scheme of this type may be that of U.S. Pat. No. 4,559,946 (Mower). In this approach, a series of relatively low-energy (0.1–15 Joules) pulses is used to successively "capture" increasing amounts of myocardium and subsequently achieve defibrillation by the succession of shocks, even though each low-energy shock might be in effective by itself for this purpose. Specifically, the configuration of the arrhythmia is "coarsened," i.e., the configuration of the arrhythmia is altered primarily by reduction of frequency or increase of amplitude. Thus, for example, ventricular fibrillation is coarsened into ventricular tachycardia or ventricular flutter, or a low amplitude ventricular tachycardia pattern is changed to a high amplitude pattern which is easier to treat. The time between pulses varies from about ten milliseconds to about five seconds, preferably eighty milliseconds to 1.5 seconds. For safety, full "backup" defibrillation capabilities (i.e., energies on the order of 30–35 Joules) are available.

U.S. Pat. No. 4,693,253 (Adams) discloses a circuit suitable for using residual energy available from the defibrillation capacitors for stimulation of the cardiac tissue if normal sinus rhythm is not promptly reestablished. The stimulation occurs after the defibrillation shock, rather than before the shock as disclosed by Mower. No specific energy levels, timing parameters, or therapeutic objectives are discussed; however, the residual energy can be used at the voltage at which it appears on the defibrillation capacitors after a shock as been delivered, or it can be reduced to unspecified lower levels. Electrode configurations are shown only schematically, but it appears that the same electrodes are used for defibrillation as for delivery of the post-defibrillation stimulation even though the latter is called "pacing."

A more comprehensive scheme is that of U.S. Pat. Nos. 5,366,485 (Kroll et al) and 5,522,853 (Kroll). The first of these two patents discloses application of either a single low-energy, long-duration pretreatment pulse or a plurality of low-energy pretreatment pulses, specifically a train of low-energy pulses, spaced away from the defibrillation pulse by a time interval. The same electrodes are used for pre-treatment and defibrillation, but it is not necessarily true that the pretreatment energy arises from the capacitors used to generate the defibrillation pulse. The goal of this particular pretreatment scheme is temporal and spatial organization of significant portions of the heart, so that the subsequent defibrillation pulse can succeed with lower energy required that would otherwise be required.

Similarly, the second patent discloses matching a series of "recruitment" pulses on the order of approximately 1 Joules per pulse to the inherent frequency of the fibrillation waveform, typically four to ten Hertz, thus successively capturing regions of fibrillating tissue and thus coordinating activation wavefronts such that a defibrillation pulse can be timed to successfully convert the fibrillation at a lower energy level. In one disclosed example, the recruitment pulses are biphasic with each phase duration less than five hundred milliseconds; a preferred configuration uses a first phase duration of approximately 300 ms and a second phase duration of approximately 200 ms. The timing of the recruitment pulses is somewhat flexible; disclosed examples include a fixed percentage (e.g., 85%) of the intrinsic fibrillation rate as determined in a variety of manners, as well as a value which dynamically varies in response to instantaneous sensing and analysis of the intrinsic fibrillation rate (as from a separate bipolar electrode). The polarity of the pulses can reverse within a train of pulses. Also, the discharge pathway of successive recruitment pulses can selectively vary within the train of pulses, and thus presumably the recruitment pulses could be delivered from electrodes not used for the subsequent defibrillation pulse.

Other schemes are those of U.S. Pat. Nos. 5,431,682 (Hedberg) and 5,464,429 (Hedberg et al.). The first of these two patents discloses application of relatively lower energy (0.4 millijoule to 20 Joules) stimulation pulses after the defibrillation pulse to enable effective pacing of the heart in the vicinity of the defibrillation electrode. The delay between the defibrillation pulse and the first post-defibrillation pulse is variable, as is the rate of the post-defibrillation pulses, which can be monophasic or biphasic.

The second patent discloses application of a series of relatively low energy (1 millijoule) pulses across the range of relative timing choices, i.e., either prior to a defibrillation shock, or between multiple defibrillation shocks, or after a defibrillation shock. The pulses are typically 20–200 ms apart. The pulses are delivered through intracardiac or epicardiac electrodes normally used for pacing. The stimulation pulses produce a refractory area around the stimulation electrode for stopping fibrillation activity.

DISCLOSURE OF INVENTION

The invention is a single electrical therapy applied to a selected region of selected cardiac tissue, comprising the combination of two discrete therapies: pacing level therapy applied to a localized portion of a region of the selected cardiac tissue having relatively low susceptibility to defibrillation-level shock field strengths; followed by (or occurring simultaneously with) defibrillation therapy applied to portions of the tissue having regions of fibrillating myocardium over which the sub-defibrillation level shocks exert control; such regions of fibrillating myocardium are those characterized by a 1:1 phase lock of a local electrogram of any region to a stimulus artifact of that region.

Thus, in another sense, the invention is the application of at least one exogenous pacing level shock to regions of fibrillating myocardium within selected cardiac tissue, any such region being characterized by a 1:1 phase lock of a local electrogram of that region to a stimulus artifact in that region, such that invasion of intrinsic fibrillation wavefronts into at least one region of fibrillating myocardium is prevented.

Regardless of how the invention is described, the advantage of the invention is that the strength (voltage and/or energy) required for successful defibrillation by the first defibrillation-level shock is reduced. This is because, while the region controlled by the pacing level shocks may be only the same size as the localized region, the goal of the method is for the successive regions of fibrillating myocardium to be successively larger in terms of the amount of tissue controlled. A successively larger amount of controlled tissue increases the probability that the entire heart may be successfully treated by a single defibrillation shock, and especially so by a single defibrillation shock of reduced strength than would be possible otherwise.

In any embodiment of the invention, the selected cardiac tissue may be ventricular tissue, or it may be atrial tissue; in the latter case, the first defibrillation shock which would otherwise occur within the vulnerable period (T-wave) of the ventricular activation cycle, should not occur until after ventricular depolarization.

The first defibrillation-level shock occurs at least as soon as (i.e., coincident with or after) the last pacing level shock; preferably, the last pacing level shock occurs not sooner than the beginning of an optimum period beginning before the first defibrillation-level shock. This period can be determined by extracting a feature from sensed cardiac signals, such as morphology of the ECG or some component of the ECG; some fraction (e.g., 80–100%) of the cardiac cycle length, etc. The exact condition used to determine the optimum period is determined empirically by the particular clinical and therapeutic context; however, typical practical limits on the optimum period would be from 250 milliseconds prior to the first defibrillation shock, to coincident (or simultaneously), i.e., within less than one millisecond, with the first defibrillation shock.

By appropriate designation of the region of selected cardiac tissue, it is possible to apply the method of the invention to the treatment of characteristically different arrhythmias, provided that the arrhythmias are convertible to other states "closer" to (if not actually the state of) normal sinus rhythm. That is, if an arrhythmia is known to be convertible to a condition of increased periodicity, then a more predictable conversion of the arrhythmia is possible. Typical conversions are to normal sinus rhythm, or to near-normal sinus rhythm[2], in a single defibrillation shock, but in multi-shock situations it is possible that the conversion will simply be to an intermediate state, i.e., one which may in turn be converted to normal sinus rhythm by application of at least one additional shock. (Near-normal sinus rhythm is itself an example of such an intermediate state.) Thus, the invention may be practiced in situations in which a plurality of different shock strength profiles is applied to a plurality of regions of the selected cardiac tissue, the regions having characteristically different arrhythmias convertible to other states by mechanisms which differ from each other. Each of the plurality of shock strength profiles is selected to correspond to each of the plurality of regions according to the ability of the profile to provide increased periodicity in each region. Use of the invention is successful if predictable activation is created in at least one particular region.

[2]In a "near-normal" sinus rhythm, the heart rate is greater than normal sinus rhythm, but the heart is hemodynamically stable.

The preferred embodiment is a series of pacing level shocks, which is readily provided by known pacing techniques.

Specific physical embodiments of the invention treat cardiac arrhythmia according to the steps of: (a) determining a region of selected cardiac tissue having relatively low susceptibility to defibrillation-level shock field strength; (b) applying at least one pacing level shock to a localized portion of the region of selected cardiac tissue; and (c) applying at least one defibrillation-level shock to the heart, but not before step (b) has occurred. Thus, the defibrillation-level shock is applied prior to or simultaneously with the last pacing level shock; but the last (i.e., the only, if a single pacing pulse is used) pacing level shock should occur within one mean activation interval prior to the first.

Thus, another aspect of the invention is a system for carrying out any of the methods described above. Such a system comprises a pulse generator subsystem capable of providing pacing level and defibrillation level shocks, and an electrode system[3] positioned with respect to the selected cardiac tissue such that the pacing level shocks may be applied to regions of the tissue where the defibrillation-level shock-induced field intensity is weak.

[3] A single, composite, or multiple member device providing the common functions of electrodes—sensing, pacing, and shocking—at the subcutaneous, epicardial, myocardial, or endocardial locations, and introduced to the cardiac tissue directly or transvenously. Electrodes can be either anodic or cathodic, as required by the application. The housing containing the pulse generator subsystem, if implantable, may itself be an electrode (anode or cathode), either as a supplemental electrode to an endocardial, myocardial, or epicardial electrode, or as a free-standing electrode.

The pulse generator subsystem may comprise separate pacing level and defibrillation level units, but devices combining these two functions into a single implantable pulse generator are preferred.

While any portion of the system other than the shocking and sensing portions of the electrodes may be external to the patient, a fully-implantable system is preferred.

DETAILED DESCRIPTION

As in the known variations on the classic "single therapy" approach to defibrillation described above, the invention is based on simultaneous or near-simultaneous combination of two therapies, pacing level shocks (~1–10 V) and defibrillation (including cardioversion) shocks (~200–800 V level). This invention utilizes both pacing level shocks and defibrillation shocks in either a temporally coincident, or an immediately sequential, fashion. The inventive therapy constitutes a hybrid, combination tachyarrhythmia therapy referred to here as "defibroversion." Defibroversion therapy is produced by applying a rapid series of pacing pulses that influence only a localized portion of selected cardiac tissue, in addition to at least one defibrillation-level shock.

Defibroversion may be implemented in any of several physical configurations. In general, defibroversion requires implantation of defibrillation electrodes in, on or near the heart such that when defibrillation-level shocks are applied, the regions of weak field intensity are located in a region that is accessible by conventional techniques for introduction and fixation of pacing electrodes in or immediately adjacent to that region. Pacing level shocks are then applied to the heart tissue in the area of the heart where the defibrillation-level shock fields are known to be weak. In this way, tissue in the weak field area is actively stimulated and locally controlled by the pacing pulses. If a suitable volume of tissue has been influenced, a defibrillation-level shock is applied at a time based on predetermined timing criteria. This provides an optimum coupling interval between the last controlled beat and the first higher level shock.

In practice, the preferred optimum coupling interval ranges from less than one millisecond (i.e., "simultaneously") to about 200–250 ms. However, because the invention is applicable to a variety of different arrhythmias, the coupling interval is best determined by optimization based upon one or more features extracted from the morphology and/or cycle length (or other timing parameters) of the cardiac rhythm as sensed prior to the defibrillation level shock.

Figure 1:
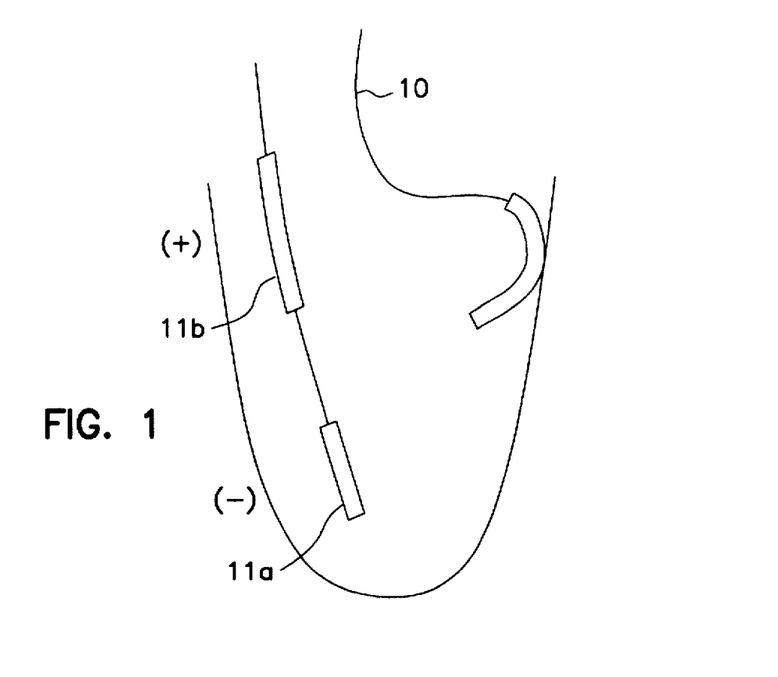
FIGS. 1–4 are schematic cross sectional views of a heart and electrodes positioned according to respective embodiments of the invention.
Figure 2:
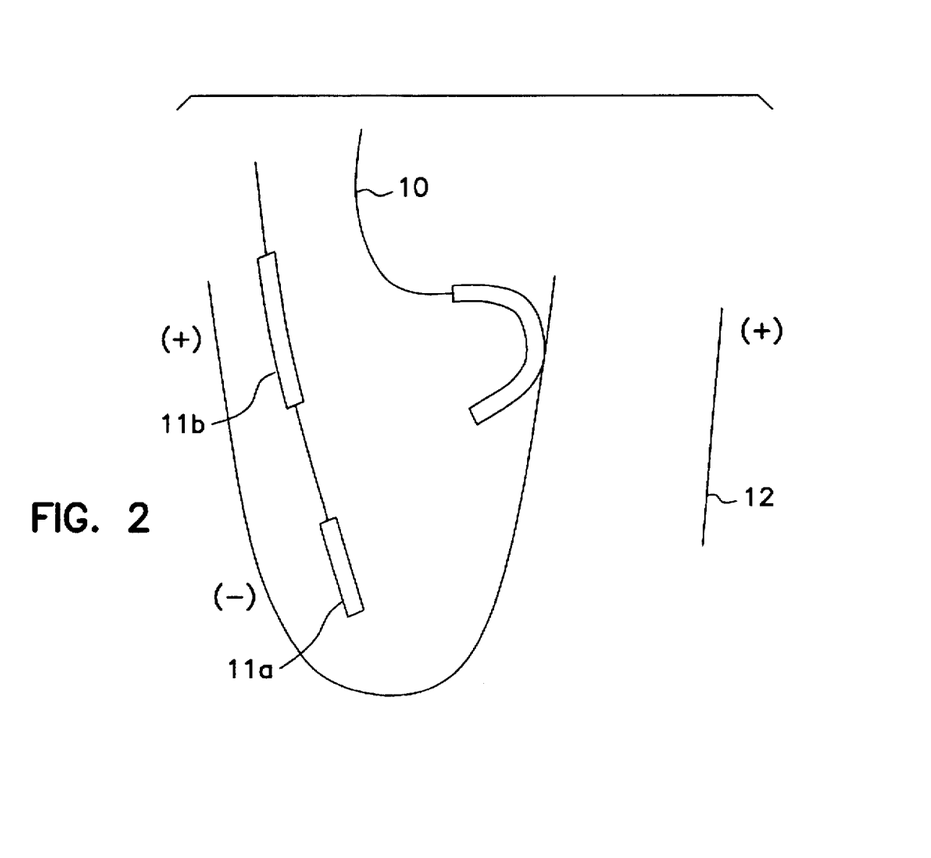

In one embodiment, as shown in FIG. 1, pacing pulses are administered from a transvenous lead (10) residing in or near the coronary sinus along the postero-basal region of the left ventricle (LV) or in the right ventricle (RV) outflow tract, while the defibrillation-level pulse is applied between endocardial electrodes (11a, 11b) residing in the RV apex (electrode 11a) and in the superior vena cava (SVC) (electrode 11b) just proximal to or partially in the right atrium. A second embodiment, as shown in FIG. 2, is identical to the first with the exception that the defibrillation-level pulse is applied along a bi-directional pathway from the (now cathodic) RV electrode (11a) to a common anode formed by two electrodes: one (11b) residing in the SVC (as before), the other (12) residing in the left lateral subcutis centered approximately on the mid-axillary line. (In this, as in other embodiments, the roles of one electrode, or set of electrodes, as the anode and the other as the cathode can be interchanged without loss of generality to the invention.) Without loss of generality, the electrode (12) located in the left lateral subcutis can be an electrically active housing of the pulse generator, as discussed in more detail below.

Figure 3:
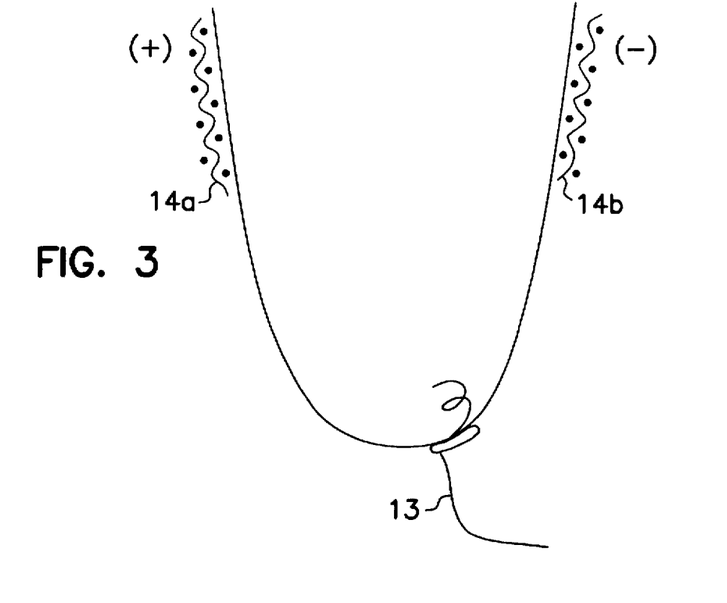

In a third embodiment, as shown in FIG. 3, the pacing-level pulses are delivered from a sutureless myocardial ("screw-in") lead (13) positioned in an apical region of the heart. Defibrillation-level pulses are applied between epicardial electrodes (14a, 14b) positioned substantially opposite each other on the free walls of the ventricles.

Figure 4:
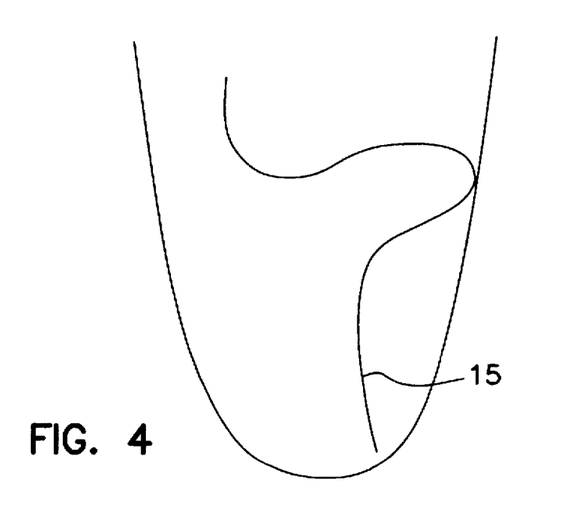

FIG. 4 shows a preferred location for a transvenous pacing electrode (15) which has been introduced into the coronary sinus, then into the great cardiac vein, and then into the ascending limb of either the anterior cardiac vein or the posterior cardiac vein, into the vasculature of the left ventricle. Because the courses of these veins are near the surface of the heart, this location gives performance very similar to that of the epicardial electrode discussed below, even though the location is within the cardiac vasculature. This embodiment places the pacing electrode (15) as close as possible to the apex of the left ventricle via a transvenous procedure, which is desirable to avoid a thoracotomy, median sternotomy, or other extensive surgical procedure.

In any of the embodiments above, an electrically active housing of the pulse generator can also serve as a defibrillation electrode, either in addition to the RV and SVC electrodes, or as a replacement to either (but typically not as a replacement for the RV electrode to ensure that sufficient ventricular mass is affected by the defibrillation shock).

Figures 5, 5A:
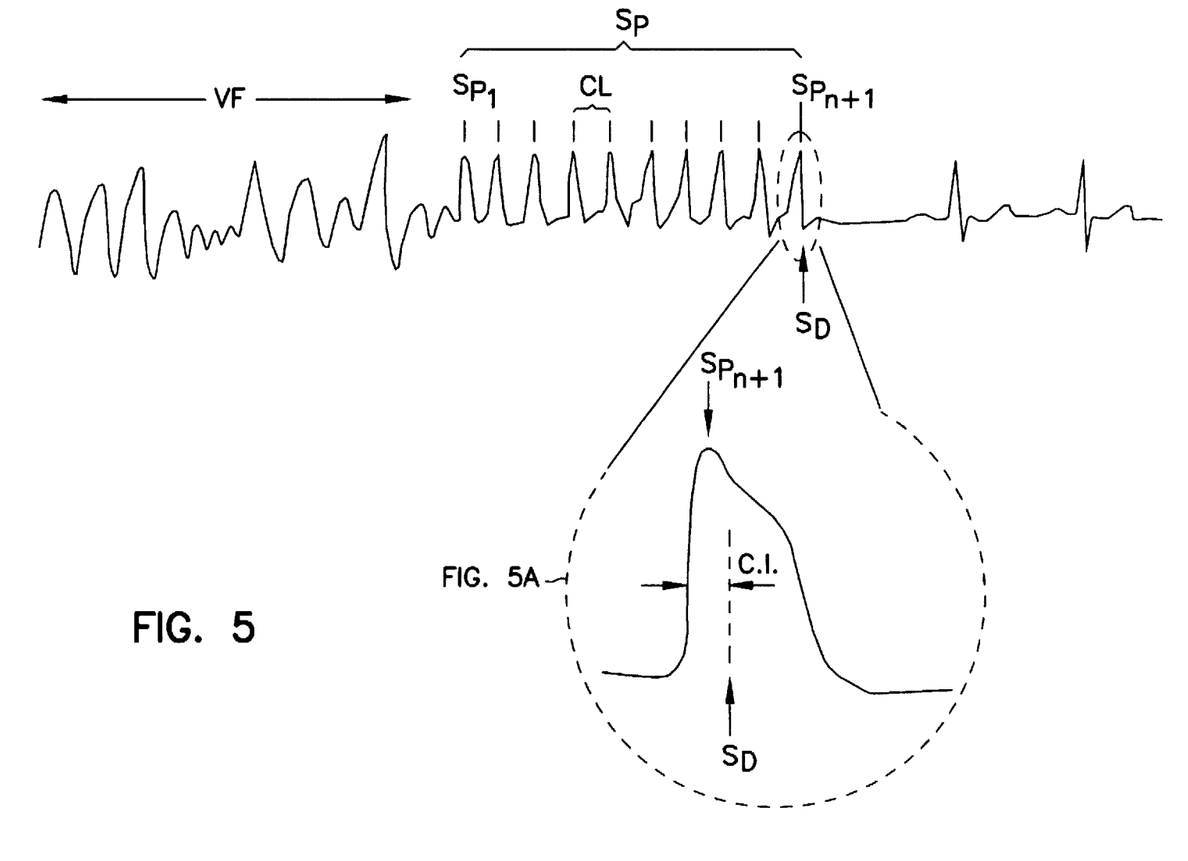
FIG. 5 is a schematic timing diagram of one embodiment of the invention.
FIG. 5A is a detail of the schematic timing diagram of FIG. 5.

The details of a scheme employing pacing-level pulses, applicable to any of the embodiments of FIGS. 1–4, are shown schematically in FIGS. 5 and 5A. The series of pacing-level pulses, denoted $S_P$, is delivered during a period of hemodynamically unstable tachyarrhythmia, denoted schematically as VF (the tachyarrhythmia need not be only ventricular fibrillation, though that is a common condition). For this illustration, the pacing pulses have a cycle length (CL) of approximately forty to ninety-five percent of the sensed cycle length of the local activations in the area of the heart in the region where the defibrillation-level shock field intensity is weak. The defibrillation shock is denoted $S_D$.

(The defibrillation shock normally but not necessarily arises from a capacitor discharge and displays a biphasic truncated exponential pulse shape. Such shocks are preferably produced by terminating the discharge waveform of a capacitor network[4] having capacitance in the range of 20–400 µF; but any otherwise suitable device for producing the shocks may be employed. For example, the method is applicable to defibrillation shocks arising from multiple-capacitor networks and/or monophasic or multiphasic pulse shapes.)

[4] A single capacitor, or multiple capacitors, as dictated by morphology, available pulse generator volume, and other considerations.

The first pacing pulse in the series is designated $S_{P1}$, while the last pulse is designated $S_{Pn+1}$, with n+1, the number of pulses, running from about ten to several hundred. During application of the series of pacing pulses, tissue is activated (or, "controlled") by the pulses when each pulse is separated by an optimum cycle length. This exogenous stimulation, in a sense, creates a local "intensified ventricular tachycardia," i.e., a rapid locally propagated rhythm with a characteristic rate that only slightly exceeds the local intrinsic rate.

However, the extent of activation is not global like that observed for pacing during normal sinus rhythm (NSR)[5]. Instead, the spatial extent of activation, or "controlled tissue volume," is bounded by tissue rendered refractory to stimulation by propagated VF wavelets from immediately adjacent tissues. If the cycle length of the pacing pulses is optimally short, the controlled tissue volume will increase as more pacing pulses are applied. In general, the controlled tissue volume represents a volume of tissue rhythmically activating while at the same time the remaining portions of the heart are fibrillating. These volumes importantly correspond to areas in which the shock-induced field intensity is weak during attempted defibrillation.

[5] Thus the term "controlled" rather than the term "captured" as commonly used in the bradycardia pacing art, but the concept behind the two terms is the same.

Figure 6:
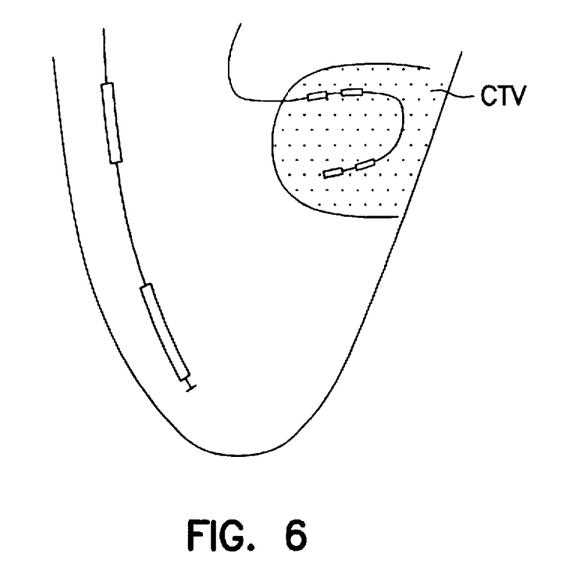
FIGS. 6, 7 and 8 are schematic cross sectional views of a heart and electrodes positioned according to respective embodiments of the invention.

Referring briefly to FIG. 6 (which shows for illustrative purposes only the electrode configuration of FIG. 1), as the critical tissue volume increases, the required strength of the defibrillation shock decreases. This is because during "defibroversion" the critical point (the region where critical field intensity intersects vulnerable state of refractoriness) is translocated from its initial location ($CP_0$) to a point ($CP_1$) closer to the interelectrode axis (16), thus increasing the effectiveness of the defibrillation-level shocks delivered by the defibrillation electrodes (11a, 11b).

Returning again to FIGS. 5 and 5A, after a number of pacing pulses preceding the last such pulse, $S_{Pn+1}$, the defibrillation-level shock $S_D$ is administered between the shocking electrodes (using, for example, any of the configurations of FIGS. 1–4) at an optimum ($S_{Pn+1}$—$S_D$) coupling interval (CI). Since the tissue in the controlled tissue volume is rhythmically activating at its optimum cycle length, stimulation during the vulnerable period can be avoided by triggering the defibrillation-level shock $S_D$ at some optimum coupling interval.

Figure 7:
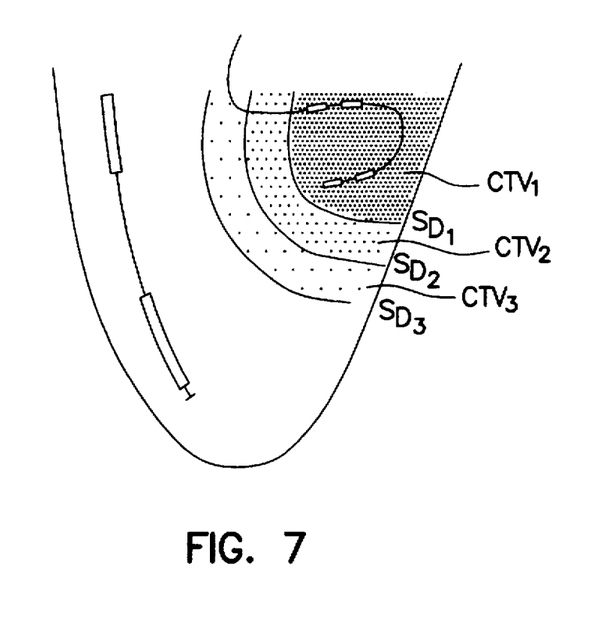

As shown schematically in FIG. 7 (which also shows for illustrative purposes only the electrode configuration of FIG. 1), multiple defibrillation-level shocks will cardiovert successive (preferably but not necessarily successively larger) amounts of controlled tissue ($CTV_{1-3}$). Adjacent regions (not shaded) are defibrillated.

Figure 8:
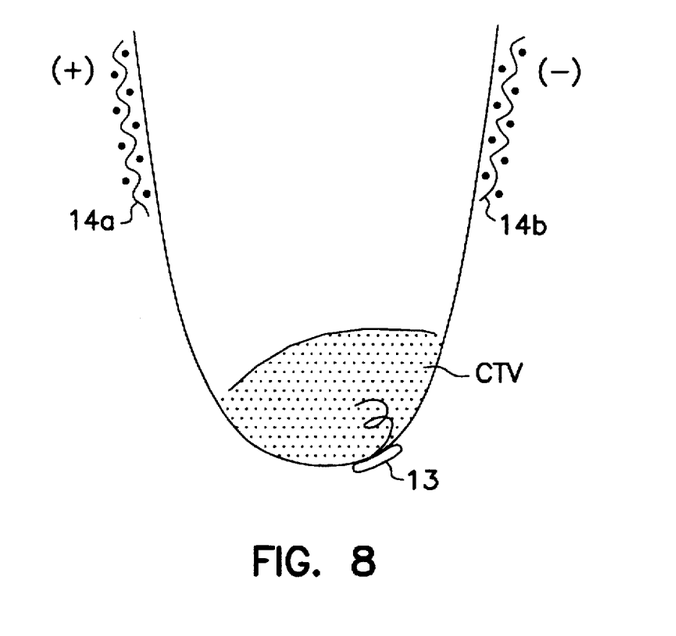

FIG. 8 shows the critical tissue volume (CTV) when epicardial defibrillation electrodes (14a, 14b) and a suture-less myocardial pacing electrode (13) are implemented, as described above in reference to FIG. 3.

Figure 9:
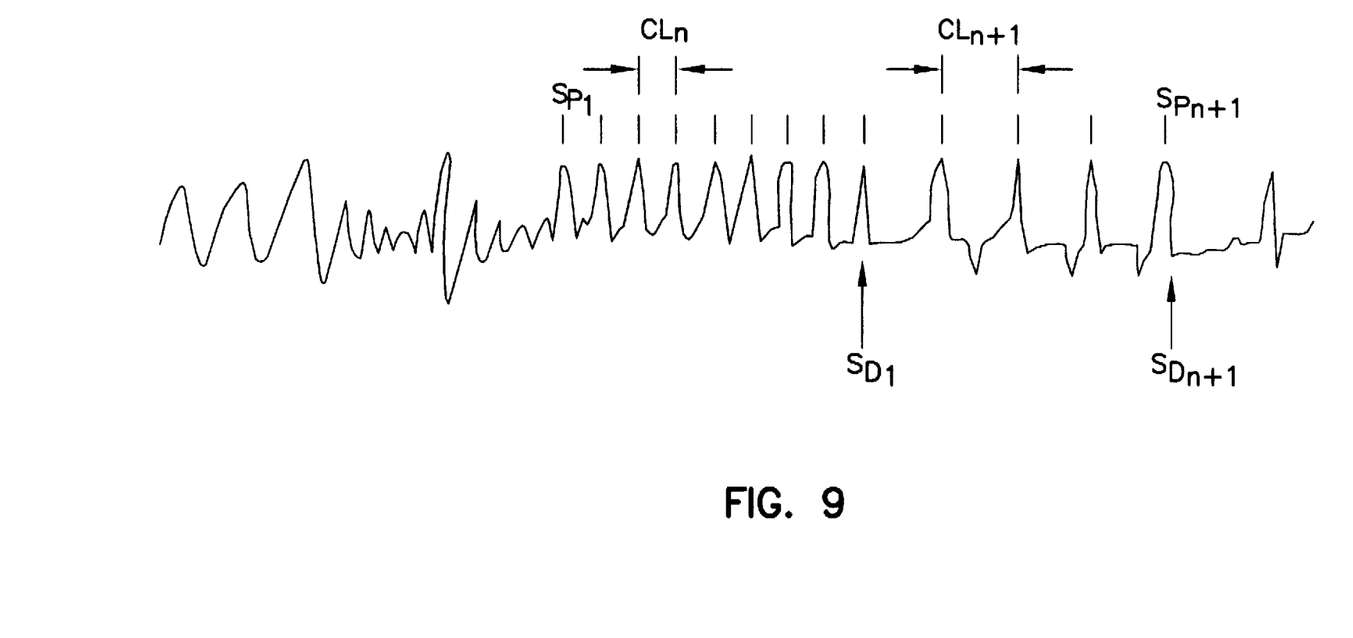
FIG. 9 is a schematic timing diagram of an alternative embodiment of the invention.

An alternative embodiment is shown schematically in FIG. 9. Multiple high-strength defibrillation-level shocks ($S_{Dn}$ through $S_{Dn+1}$) are given after the first of a series of multiple applications of pacing-level pulses ($S_{P1}$ through $S_{Pn+1}$). The first defibrillation-level shock ($S_{Dn}$) fails to defibrillate the entire heart. However, the vulnerable tissue located adjacent to the controlled tissue volume border, and thus in areas where the defibrillation shock field intensity is weak, is stimulated by the propagated impulses emanating from the closely adjacent regions directly excited by the first defibrillation-level shock ($S_{D1}$). Tissue in the controlled tissue volume is cardioverted and simultaneously recovers excitability over a time period approximately equal to the mean intrinsic activation interval, as measured immediately prior to the shock, after application of the first defibrillation-level shock ($S_{D1}$). (The mean activation interval is preferably determined from the average of from about three to ten activation intervals.) As a result, continued application of pacing-level pulses ($S_{P1}$ through $S_{P+1}$), just prior to the first intrinsic beat, controls the tissue in the original controlled tissue volume; it subsequently increases the extent of the controlled tissue volume as more tissue comes under direct influence of the rapid pacing in areas where the defibrillation-level field strength is weak (cf. FIG. 7). In this way, synchronization of multiple defibrillation-level shocks is employed to cardiovert progressively larger volumes of tissue until the potentially lethal arrhythmia is terminated, a process referred to as "deceleration" of the tachyarrhythmia.

An alternative approach to deceleration of the tachyarrhythmia is also depicted in FIG. 9. The original cycle length of the pacing pulses ($CL_n$) is relatively close to the cycle length of the local activations of the fibrillating tissues in the weak field area. After application of the first defibrillation-level shock ($S_{D1}$), a new and longer cycle length ($CL_{n+1}$) (i.e., a slower rate) is used to control the critical tissue volume. After each successive defibrillation-level pulse ($S_{D2}$ to $S_{Dn+1}$) the succeeding cycle length of the pacing pulses is reduced by an amount which is preferably, but not necessarily, programmable.

One explanation of the mechanism illustrated in FIG. 9 considers the traditional view that in defibrillation, most or all of the heart must be subjected to a minimum shock-induced voltage gradient. However, since the heart is geometrically asymmetric, higher shock strengths are required to create the minimum gradient in regions distant from the electrodes than would be required otherwise. Increasing the shock strength gradients in these remote regions accounts for the major portion of "wasted" shock strength, and also contributes to the highly non-uniform gradient distribution throughout the ventricles, which is often on the order of 30:1. In contrast, if the heart were perfectly spherical and the electrodes were diametrically opposed from each other, then shock strengths required for defibrillation would be reduced. Thus, by practicing the invention, defibrillation shock strengths required for effective defibrillation decrease, because the geometrically remote regions are effectively cardioverted, and therefore do not have to be boosted above the critical minimum for direct stimulation. However, it is important to remember that the pacing level shocks are not cardioversion shocks per se, because of their reduced voltage/energy level compared to cardioversion shocks.

With no loss of generality in the scope of the invention, the scenarios above can be modified. For example, it is possible to intersperse one or more series of pacing pulses having different parameters such as voltage, energy, polarity, etc. This would be done in combinations dictated by the success of either type of pacing level shock in exerting control over sufficient fibrillating myocardium to ensure successful defibrillation by the defibrillation-level shock or shocks.

The inventive method is applicable to atrial arrhythmias in addition to the ventricular arrhythmias described above. In atrial applications, the time at which the defibrillation shock is applied is extremely critical, because stimulation during the ventricular vulnerable period (T-wave) could initiate ventricular fibrillation. Consequently, implementation of the method further requires measures to assure that the defibrillation shock is always applied immediately following ventricular depolarization. Since the initiation of the pacing level shock is not coupled to ventricular activity, the last pacing level shock (i.e., the shock occurring just prior to the defibrillation shock) cannot be assured to correspond to a safe (non-vulnerable) state of ventricular activity. Therefore, in a preferred embodiment, once an atrial arrhythmia is declared and after delivery of a preselected (preferably but not necessarily programmable) number of pacing level shock(s), a comparator looks at temporal inputs from a ventricular activation sensor (such as could be located in the apex of the right ventricle), and the time of the pacing level shock, and determines when a safe condition exists to deliver a defibrillation pulse. In this way, any pacing level shock is not delivered until the comparator finds a time when a ventricular activation falls within a pre-established optimum temporal window surrounding the pacing level shock.

Especially preferred in the atrial application, but applicable to ventricular applications, is the application of pacing-level shocks followed by at least one additional sub-defibrillation-level shock (either an additional series of pacing-level shocks, or shocks having waveforms congruent with defibrillation-level shocks but reduced in strength from defibrillation shocks), prior to the first defibrillation-level shock. For example, a first series of pacing pulses (having a first cycle length) may bring a region of tissue under control, and then be followed by a sub-defibrillation-level shock that brings additional tissue under control. At this point, a defibrillation-level shock may be appropriate; but, if not, a second series of pacing-level shocks may be applied. The second series of pacing-level shocks may, but need not necessarily, have any or all of the same total duration, polarity, phase, amplitude, etc. that the first series of pacing-level shocks had, as dictated by clinical considerations. However, since the region of controlled tissue is increasing, the cycle length of the second pacing-level shocks will be greater than or equal to that of the first series of pacing-level shocks. The entire process may be repeated until a defibrillation-level shock is applied to bring the heart to normal sinus rhythm.

Figure 10:
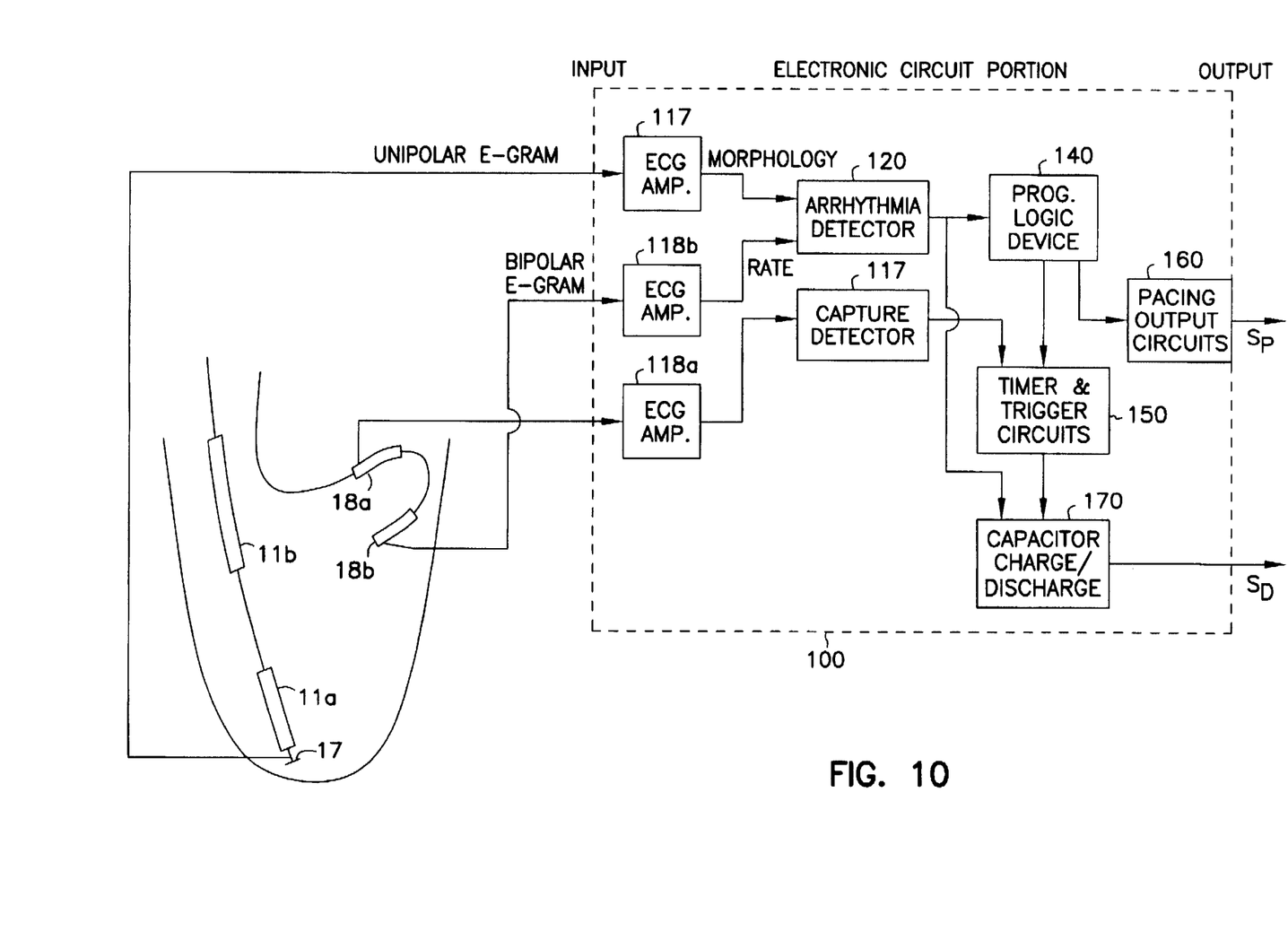
FIG. 10 is a schematic block diagram of a system embodiment of the invention.

FIG. 10 illustrates schematically one of the possible system embodiments of the invention, implementing again, for illustrative purposes only, the electrode configuration of FIG. 1 and employing the pacing-level shocks described above. In this preferred embodiment as shown, an additional "tip" electrode (17) is added to the electrode system comprising the defibrillation electrodes (11a, 11b). The additional tip electrode (17) provides a unipolar electrogram for the morphology detection component described below. The coronary sinus electrode system comprises two electrodes (18a, 18b) which each provide bipolar electrograms as described below.

The pulse generator system (100) comprises subsystems, components and electronic components shown schematically within the dotted line. Inputs from the electrodes (17, 18a, and 18b) go to their respective ECG amplifiers (117, 118a, and 118b), the outputs of which are used for additional processing. The unipolar electrogram from the tip electrode (17) provides morphology data; the bipolar electrogram from the distal (as illustrated) coronary sinus electrode (18b) provides rate data. These two inputs are processed by an arrhythmia detector (120) (any arrangement providing clinically useful arrhythmia detection is suitable). The other bipolar electrogram from the proximal (as illustrated) coronary sinus electrode (18a) is processed by a capture detector (130) (any arrangement providing clinically successful capture detection is suitable).

The outputs of the arrhythmia and capture detectors (120, 130) are the inputs to appropriate processing circuitry as shown. The arrhythmia detector (120) output goes in parallel to a preferred programmable logic device (140) which produces the pacing-level signal logic required; and additionally to the capacitor network charge/discharge controller (170) which produces the defibrillation-level signal logic required. The programmable logic device (140) also drives timing/trigger circuitry (150), as does the output of the capture detector (130). The output of the timing/trigger circuitry (150) is another input to the capacitor network charge/discharge controller (170).

The pacing output circuit (160) and capacitor network charge/discharge controller (170) provide the pacing-level shocks ($S_P$) and defibrillation-level shocks ($S_D$) through appropriate electrode systems to the coronary sinus electrode (10) and defibrillation electrodes (11a, 11b).

Of course, not shown in FIG. 10 but well within the skill of the art to supply, are power supplies, implantable housings and other materials for the pulse generator (100) and electrode systems (10, etc.), general timing, memory, and support circuitry, and the like.

The principles described above regarding use of alternate electrode configurations (such as those shown in FIGS. 2–4), multiple defibrillation-level shocks, etc., can all be incorporated (in whatever combination is required) by the skilled artisan into system embodiments, like that of FIG. 10, without undue experimentation.

In confirmation of the underlying principles of the invention, experimental data indicates that rapid pacing pulses imposed during ventricular fibrillation produce local control of the myocardial tissue. Two pacing electrodes (5 mm separation) were placed flush with the epicardium of the anterobasal right ventricle of swine (N=6, 25–30 kg) anesthetized with pentobarbital. Pledgeted sutures held a plaque such that 506 electrodes (composition: an alloy of silver and silver chloride; diameter: 125 µm) embedded in the plaque in a 22×23 pattern at 1.12 mm spacing, were flush with the epicardium. The plaque was positioned such that the pacing electrodes were approximately centered beneath it. Extracellular unipolar potentials (referenced to the left leg) were bandpass filtered between 0.5 and 500 Hz, sampled at 2 KHz (14-bit resolution, 9.766 µV step size) and recorded on video tape with a 528-channel cardiac mapping system.

The pacing pulses comprised trains of forty (2 ms duration) rectangular monophasic stimuli applied in bipolar mode to the pacing electrodes. The trains provided a variety of coupling intervals between intrinsic ventricular fibrillation activations and the pacing pulses. To span the intrinsic activation rate during ventricular fibrillation, approximately 125 ms, a range of pacing cycle lengths of 100–140 ms was used. Stimulus strength was 10 mA, at least ten times the diastolic threshold, in an attempt to excite partially refractory tissue close to the electrodes. Pacing stimulus thresholds were determined to the nearest 0.1 mA in each swine.

Ventricular fibrillation was induced by application of 60 Hz alternating current for 1–2 seconds between a pacing electrode sutured to the epicardium of the right ventricular apex and an indifferent electrode off the heart. Two trains of forty shocks with the same cycle length were applied, the first train coming two seconds after induction of ventricular fibrillation, the second coming two to three seconds after the end of the first train. Nine pacing cycle lengths (100–140 ms, 5 ms steps) were tested in random order, each followed by termination of the ventricular fibrillation and repetition of the procedure until all nine were tested.

Evidence of local control was determined by animating 5-point dV/dt (2 frames/ms) of the extracellular potentials displayed as 22×23 arrays of black/gray/white points, each point in the array representing one of the five hundred and six electrode locations. Qualitative examination of the displayed arrays showed that when pacing stimulus occurred with a long coupling interval after the previous activation of ventricular fibrillation at the pacing site, the stimulus produced activation fronts that propagated away from the pacing site. If the tissue adjacent to the pacing site then remained inactivated until the next stimulus was applied, the next stimulus also generated an activation front that was 1:1 phase locked with the stimulus artifact. As the number of phase locked beats increased, the area of controlled myocardium increased. However, when the pacing cycle length was too long, intrinsic ventricular fibrillation activation fronts activated the tissue at the pacing site before the next stimulus was applied, periodicity was lost, and subsequent stimuli did not control the tissue. When pacing evoked 1:1 phase locking over major portions of the plaque, clearly observable differences in activation patterns were present when compared to either ventricular fibrillation without pacing or with pacing but absent phase locked beats.

In all six swine, local control was observed when the pacing shock fell late in the local intrinsic activation interval of the selected cardiac tissue immediately adjacent to the pacing electrodes. While this 1:1 phase locking of the extracellular electrogram to the stimulus artifact was observed in every swine, the spatial extent of control was not the same for all episodes within animals or between animals. In five of six swine, evidence of sustained control, taken to be five or more beats, occurred only when the pacing cycle length was 80–115% of the local intrinsic activation rate. (Because this is similar to coupling intervals for capture during atrial fibrillation and in functionally defined circuits of tachyarrhythmias, from this result alone it is quite reasonable to conclude that the invention is applicable to such conditions.) This represented twenty-five of the one hundred and eight trials. On average, 4±1.5 episodes of sustained phase locking in each swine was observed, and the mean number of controlled cycles was 18±11. In nine of the twenty-five episodes, periodicity within the phase locked region was suddenly disrupted when tissue adjacent the pacing electrodes activated immediately prior to a stimulus. In the remaining sixteen episodes, phase locking was sustained until the pacing ended, and in nine of those episodes, the number of phase locked beats was 20. In one episode (120 ms pacing cycle length), all forty stimuli produced 1:1 phase locking, with a total duration of 4.8 seconds. Within each pacing burst with sustained phase locking, the mean number of pacing stimuli applied prior to phase locking was 15±10. Phase locking was significantly more frequent ($p<0.05$ by $\chi^2$ test) during the second pacing burst (eighteen of twenty-five episodes) than during the first pacing burst (seven of twenty-five episodes).

Two independent methods quantified the 1:1 phase locking. The first was a comparison of the means and variances of the interbeat intervals during three types of qualitatively identified behavior: unpaced ventricular fibrillation; pacing when the animation provided no evidence of phase locking to the stimuli; and 1:1 phase locking between the stimulus artifact and the local electrograms. The comparison was performed by assessing the location and dispersion of Poincaré maps relating the interbeat intervals ($I_n$) to the previous interval ($I_{n-1}$) for a recording electrode at the plaque border. Representative episodes (duration approximately eight seconds) containing all three types of behavior were selected for each swine. For each episode, time series from two electrodes near the plaque border were partitioned into three sub-series corresponding to each type of behavior. The mean interbeat interval I and its standard deviation were calculated for each sub-series; outlying intervals (I<70 ms or I>170 ms) were excluded. One representative Poincaré section showed that during ventricular fibrillation, I varied for pacing pulses without local control and after pacing pulses ended, but was tightly clustered about the line of identity at the pacing cycle length (115 ms) during local control (0, 115±1 ms).

The second independent verification method was Karhunen-Loeve decomposition. The onset of pacing followed by qualitative declaration of control over the tissue was clearly associated with a marked increase in the fractional amount of total energy contained in only the first two orthogonal spatial modes; such increase is associated with higher spatial order, which indicates behavior which is repetitive and organized over its whole extent. Such results were consistent for episodes from all swine.

Thus, activation was synchronized over a significant portion (4–5 cm$^2$) of the right ventricular epicardium during ventricular fibrillation by delivering pacing pulses at or near the local intrinsic activation rate.

Additional details are in KenKnight et al., "Regional Capture of Fibrillating Ventricular Myocardium," *Circulation Research*, 77(4), 849–855 (October 1995), which is incorporated by reference.

I claim:

1. A method of treating cardiac arrhythmia, comprising application by an implantable pacing electrode system of at least one exogenous pacing level shock to at least one region of fibrillating myocardium of selected cardiac tissue, any such region being characterized by a 1:1 phase lock of a local electrogram of that region to a stimulus artifact in that region, such that invasion of intrinsic fibrillation wavefronts into at least one region of fibrillating myocardium is prevented.

2. A method of applying therapeutic electrical energy to a heart, comprising application by an implantable pacing electrode system of a plurality of different shock strength profiles corresponding to at least one pacing level shock strength to a plurality of regions of selected cardiac tissue, in which the regions have characteristically different arrhythmias convertible to other states by mechanisms which differ from each other, and selecting each of the plurality of shock strength profiles to correspond to each of the plurality of regions according to ability of the profile to provide increased periodicity in each region, such that predictable activation is created in at least one particular region.

3. The method of claim 2, in which the predictable activation is conversion to normal sinus rhythm.

4. The method of claim 2, in which the predictable activation is conversion to a state which may in turn be converted to normal sinus rhythm by application of at least one defibrillation-level shock.

5. The method of claim 4, in which the predictable activation is conversion to near-normal sinus rhythm.

6. A method of treating cardiac arrhythmia, comprising the steps of applying at least one pacing level shock to selected cardiac tissue having a relatively low susceptibility to defibrillation-level shock field strength by an implantable pacing level electrode system to create a predictable repolarization state, followed by activating the selected cardiac tissue in a periodic manner to reduce shock strength requirements of a defibrillation-level shock subsequently applied to the selected cardiac tissue by a separate implantable defibrillation electrode system.

7. A method of treating cardiac arrhythmia, comprising the steps of:
   (a) determining a region of selected cardiac tissue having relatively low susceptibility to defibrillation-level shock field strength,
   (b) applying a plurality of pacing pulses to the region of selected cardiac tissue by an implantable sub-defibrillation level electrode system, and
   (c) applying at least one defibrillation-level shock to the selected cardiac tissue by a separate implantable defibrillation electrode system coincident with or after a last pacing pulse.

8. A method of treating cardiac arrhythmia in which, coincident with or after the application of a first defibrillation-level shock to a heart, at least one pacing pulse is applied by an implantable pacing electrode system to a localized portion of a region of selected cardiac tissue having relatively low susceptibility to a defibrillation-level shock field strength, to reduce the strength required for the first defibrillation-level shock to defibrillate the heart by a separate implantable defibrillation electrode system.

9. A method of treating cardiac arrhythmia, comprising the steps of applying a series of pacing pulses to selected cardiac tissue having a relatively low susceptibility to defibrillation-level shock field strength, and application of at least one sub-defibrillation-level shock to the selected cardiac tissue by an implantable sub-defibrillation level electrode system, in which a first sub-defibrillation level shock occurs coincident with or after the application of a last of the series of pacing-level shocks.

10. A method of treating cardiac arrhythmia, comprising application of at least one pacing pulse to selected cardiac tissue by an implantable pacing electrode system, and coordinating delivery of at least one defibrillation shock by a separate implantable defibrillation level electrode system to the pacing pulse applied in at least one area of the selected cardiac tissue where the electric field intensity induced by the defibrillation-level shock is weak, and controlling timing of a last pacing pulse to occur coincident with or after a first defibrillation-level shock.

11. A method of treating cardiac arrhythmia, comprising applying at least one pacing pulse by an implantable pacing electrode system to exert control over fibrillating myocardium located in selected cardiac tissue having a relatively low susceptibility to defibrillation-level shock field strength, and controlling timing of a last repetition of an applied pacing pulse to occur coincident with or after a first defibrillation-level shock is delivered by an implantable defibrillation electrode system.

12. The method of claim 11, in which more than one pacing pulse is applied to produce control exerted over successive regions of fibrillating myocardium.

13. The method of claim 11, in which the application of any pacing pulse produces a region of fibrillating myocardium characterized by a 1:1 phase lock of a local electrogram to a stimulus artifact of that region.

14. The method of any of claims 7, 9, 10, or 11, in which the pacing pulse is applied prior to the application of the first defibrillation-level shock.

15. The method of claim 14 in which a last pacing pulse occurs within about one mean activation interval, calculated immediately prior to a first sub-defibrillation-level shock, from the first defibrillation-level shock.

16. The method of any of claims 7, 8, 9, 10, or 11, in which the pacing pulse is applied simultaneously with the application of the first defibrillation-level shock.

17. The method of any of claims 1, 2, 6, 7, 8, 9, 10, or 11, in which the selected cardiac tissue is ventricular tissue.

18. The method of any of claims 1, 2, 6, 7, 8, 9, 10, or 11, in which the selected cardiac tissue is atrial tissue, and the method further comprises postponing application of any defibrillation-level shock which would occur within the T-wave of ventricular activation cycle until after ventricular depolarization.

19. A system for applying therapeutic electrical energy to a heart, comprising a first generator of a plurality of pacing pulses, a second generator of at least one defibrillation-level shock, a first electrode system coupled to the first generator for delivering the pacing pulses to a first location including at least a region of selected cardiac tissue having a relatively low susceptibility to defibrillation-level shock field strength, a second electrode system coupled to the second generator for delivering the defibrillation-level shock to the heart from a second location, in which the system further comprises timers which control delivery of a first defibrillation-level shock to occur coincident with or after the delivery of a last pacing pulse.

20. The system of claim 19 in which the system applies the first pacing pulse prior to when the system applies the first defibrillation shock.

21. The system of claim 19 in which a last pacing pulse occurs within about one mean activation interval, calculated immediately prior to a first pacing pulse, from the first defibrillation shock.

22. The system of claim 19 in which the last pacing pulse is applied simultaneously with the application of the first defibrillation shock.

23. The system of claim 19 in which the selected cardiac tissue is ventricular tissue.

24. The system of claim 19 in which the selected cardiac tissue is atrial tissue, and the timers further postpone application of any defibrillation-level shock which would occur within the T-wave of ventricular activation cycle until after ventricular depolarization.

25. The system of claim 19, in which the second generator further includes a capacitor network, where the capacitor network has a capacitance in the range of 20 to 400 µF, and where the second generator generates at least one sub-defibrillation-level shock having morphology congruent with a defibrillation-level shock but strength below a defibrillation threshold of the selected cardiac tissue, by terminating the discharge waveform of the capacitor network.

26. The system of claim 25 in which the at least one sub-defibrillation-level shock is a pacing-level shock.

27. The system of claim 25, in which the capacitor network comprises at least one capacitor used for applying at least one defibrillation-level shock.

28. The system of claim 19 in which the first and second generators are combined into a single implantable device.

* * * * *